United States Patent [19]
McClain

[11] Patent Number: 5,664,593
[45] Date of Patent: Sep. 9, 1997

[54] APPARATUS FOR APPLYING SUNTANNING LOTION MIST

[76] Inventor: Edward T. McClain, 416 Park Place Ave., Bradley Beach, N.J. 07720

[21] Appl. No.: 546,552

[22] Filed: Oct. 20, 1995

Related U.S. Application Data

[63] Continuation-in-part of Ser. No. 161,803, Dec. 6, 1993, Pat. No. 5,460,192.

[51] Int. Cl.$^6$ ..................................................... A61H 33/06
[52] U.S. Cl. .......................... 132/333; 601/160; 600/21; 4/525; 4/597; 4/603; 119/604; 119/671
[58] Field of Search ...................... 132/320, 333; 4/524, 525, 528, 531, 596, 597, 602, 603, 611, 612, 615, 616; 119/604, 665, 666, 667, 668, 669, 670, 671, 678; 604/19; 601/154, 155, 156, 160; 600/21

[56] References Cited

U.S. PATENT DOCUMENTS

| | | | |
|---|---|---|---|
| 871,074 | 11/1907 | Stockton | 4/524 |
| 3,734,058 | 5/1973 | Hightower et al. | 119/665 |
| 3,867,906 | 2/1975 | Johnson | 119/671 |
| 4,056,078 | 11/1977 | Blafford et al. | 119/671 |
| 4,425,672 | 1/1984 | Johnson et al. | 4/596 |
| 4,510,889 | 4/1985 | Jobe | 119/669 |
| 4,765,542 | 8/1988 | Carlson | 4/602 |
| 5,493,996 | 2/1996 | Verschuere et al. | 119/604 |

Primary Examiner—Todd E. Manahan
Attorney, Agent, or Firm—Martin J. Spellman, Jr.

[57] ABSTRACT

An apparatus for applying suntan lotion including a liquid tight enclosure of generally cylindrical shape. The upper wall portions are tilted inwardly to form a central neck enclosure. A door in side walls of the enclosure is spring biased to the closed position. Lotion mist ports are disposed about the interior of the enclosure and supplied from a lotion distribution tube which in turn is supplied from at least one atomizing nozzle. A pump pumps the liquid lotion from a supply dispenser to the atomizing nozzles. As the lotion is pumped through the atomizing nozzle, it is formed into mist droplets which are communicated to the distribution pipe and then to the mist outlets in the chamber. The droplets contact the body of the person in the chamber and are applied to the skin in that manner. A recirculating pump is provided for evacuating the misted droplets and to recirculate them into the distribution tube by means of an impeller fan. Lotion which may condense inside the impeller is stored in a used lotion recovery reservoir. The pump and motor which drives the pump and empeller fan is operated by token operator control located outside the enclosure.

1 Claim, 8 Drawing Sheets

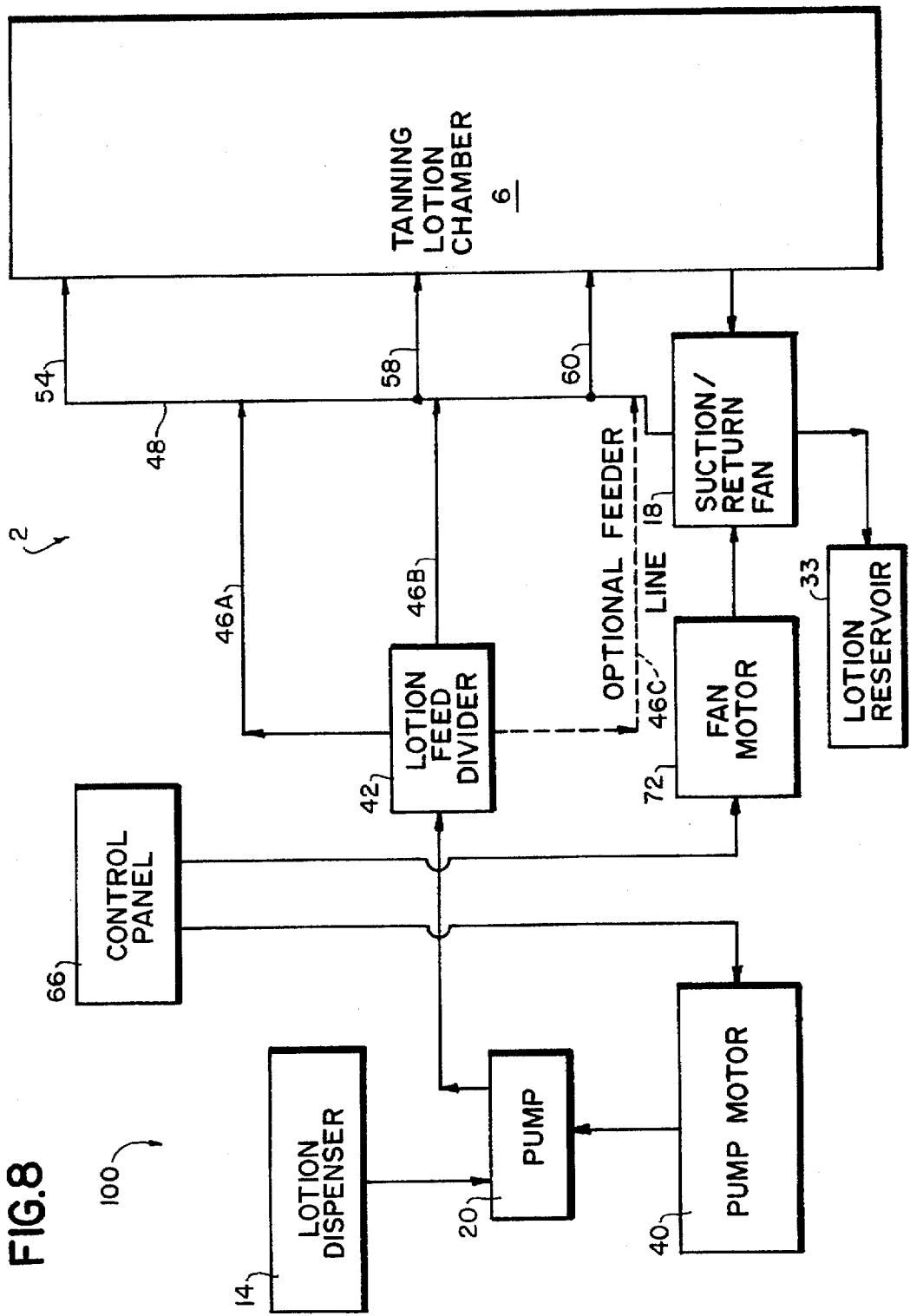

5,664,593

APPARATUS FOR APPLYING SUNTANNING LOTION MIST

CROSS REFERENCE TO RELATED APPLICATION

This application is a continuation-in-part application of my prior application Ser. No. 08/161,803 filed Dec. 6, 1993, now U.S. Pat. No. 5,460,192 issued Oct. 24, 1995.

BACKGROUND OF THE INVENTION

1. Field of the Invention

This invention is concerned with apparatus for conveniently and neatly applying suntan lotion to the entire body, automatically and efficiently. The apparatus uniformly distributes the lotion over the skin surface of the user in a few seconds. The term suntan lotion is meant to include emollient forms of conventional tanning lotion and the now widely used blocking screen lotions. The latter prevent burning and tanning of the skin with the resulting damage to the skin cells which lead not only to painful burns, and in some cases blistering, but often to long term deleterious effects on the skin, including skin cancer.

It is now well known that undue exposure to the ultraviolet rays of the sun greatly increases the probability of the individual developing skin cancer, often years subsequent to the exposure to the burning rays of the sun.

The present protective lotions currently are applied by individual users usually from a jar or a squeeze tube container either in globs on a skin surface or in the palm of the hand and the lotion subsequently spread on other parts of the body. This generally results in very uneven application, often missing certain hard to reach areas of the skin, as well as requiring the wasteful dispensing of multiple portions of the lotion during the application process. In addition, it is often applied on the beach and users are exposed to getting sand stuck to their hands or other portions of the body where the lotion is applied and dries on the skin. This causes great annoyance and discomfort.

On occasion, individuals forget to bring lotion with them and either are forced to borrow from a companion or to risk a severe burn and exposure to dangerous ultra violet solar rays for that day.

The apparatus of the present invention is designed to be located at the beach or other suntanning areas to provide a way of uniformly dispensing sun tan lotion by spraying it evenly on the body of the user in a rapid, convenient, and inexpensive manner. The apparatus most often would be controlled by a coin operated or bill actuator installed on or adjacent the apparatus. The apparatus comprises a specifically designed enclosure for the user's body, except for the head, having lotion dispensing spray nozzles appropriately located and mounted against the inner walls of the apparatus, a pump for supplying lotion to the enclosure through distribution pipes and spray heads, a reservoir for the lotion, and associated controller and motor.

2. Prior Art

There is no apparatus presently on the market or known that is specifically designed for applying suntan lotion or sun tan blocking lotion uniformly to the skin of the user.

Of remote background interest are U.S. Pat. No. 157,846, Leslie and U.S. Pat. No. 582,639, Gray which disclose cabinets which enclose the human body for purposes of applying vapor or steam baths. U.S. Pat. No. 3,590,398, Jettar and U.S. Pat. No. 5,216,763, Grenier disclose portable shower arrangements wherein the person using the device stands in the inside the enclosure while shower Water is Supplied through appropriate dispensing nozzles at the upper end of the device.

U.S. Pat. No. 4,862,526, Berger discloses an enclosure wherein vapors contact the body as the user sits within the enclosure.

SUMMARY OF THE INVENTION

This invention comprises an apparatus for uniformly applying suntan lotion to the user's torso and limbs by a token operated mechanism. The apparatus comprises a base platform having a drain aperture, a recess for retaining a grid on which the user stands, and means for securing the enclosure portion of the apparatus and supporting the associated pump, a circulating fan with screen, storage containers, motor and controls which are generally stored exteriorly of the apparatus enclosure.

The enclosure is generally of an upright cylindrical shape with one open end secured to the base and the top end tapering inwardly to a neck enclosure for the user at the top.

One portion of the exterior walls of the container serves as a closely fitting door opening. The door is provided with spring biased hinges and preferably is mounted on a piano type of hinge that is vertically oriented.

Lotion mist ports are located at approximately shoulder and waist height, and in the area of the legs. They are supplied by distribution tubing and an atomizing nozzle.

The circulating fan and tube join a supply pipe from a pump, to a nozzle, supply reservoir for the lotion, a motor to drive the pump, and associated controls that are connected to controls utilized by the user that are mounted on the exterior of the enclosure nearby the door.

A suitable pump is one typically used for atomizing oil into the fire chamber of a furnace and driven by horsepower 60 Hz motor. The pressure utilized is adjusted according to viscosity of the lotion to atomize said lotion into the forced air stream in the tube.

The device of my prior application, although very effective, used significant amounts of lotion since it was applied to the user from spray nozzles to which it was pumped into liquid form.

In my current invention, the lotion is pumped through atomization nozzles Similar to that used in oil burner injection nozzles, and then carried into a moving air stream to outlets or orifices in the enclosure by means of a distribution pipe. The lotion is maintained in mist form and emitted from the outlet openings into the chamber where the fine mist of lotion covers the user. Most of the mist which does not land on the user and does not condense out is recirculated through a suction fan and impeller which entrains the lotion mist in the atomization stream. In the blower section, lotion that condenses out is recovered. Any lotion mist condensing along the walls of the chamber is removed through the usual drain pipe at the base of the enclosure.

This method obtains complete uniform coverage of the user in a much shorter time than the simple spray method and utilizes significantly less amounts of the lotion.

The floor of the base is tilted towards a drain hole so that the excess lotion which condenses in the enclosure chamber may drain out and the interior of the enclosure may be readily flushed out with water and/or other cleaning fluid whenever cleaning is necessary. It is not required to clean the device very often because the orientation of the distribution nozzles assures that most of the lotion is applied to the user's torso and limbs and that there is very little overspray. In use, any excess applied to user's body may be wiped off with the user's hands and applied to user's face and ears, neck and the like which are not within the spraying field.

BRIEF DESCRIPTION OF THE DRAWING

In the accompanying drawing which forms of a part of the specification:

FIG. 8 is a schematic diagram of the components of the apparatus.

ILLUSTRATIVE SPECIFIC EMBODIMENT

Figure 1:
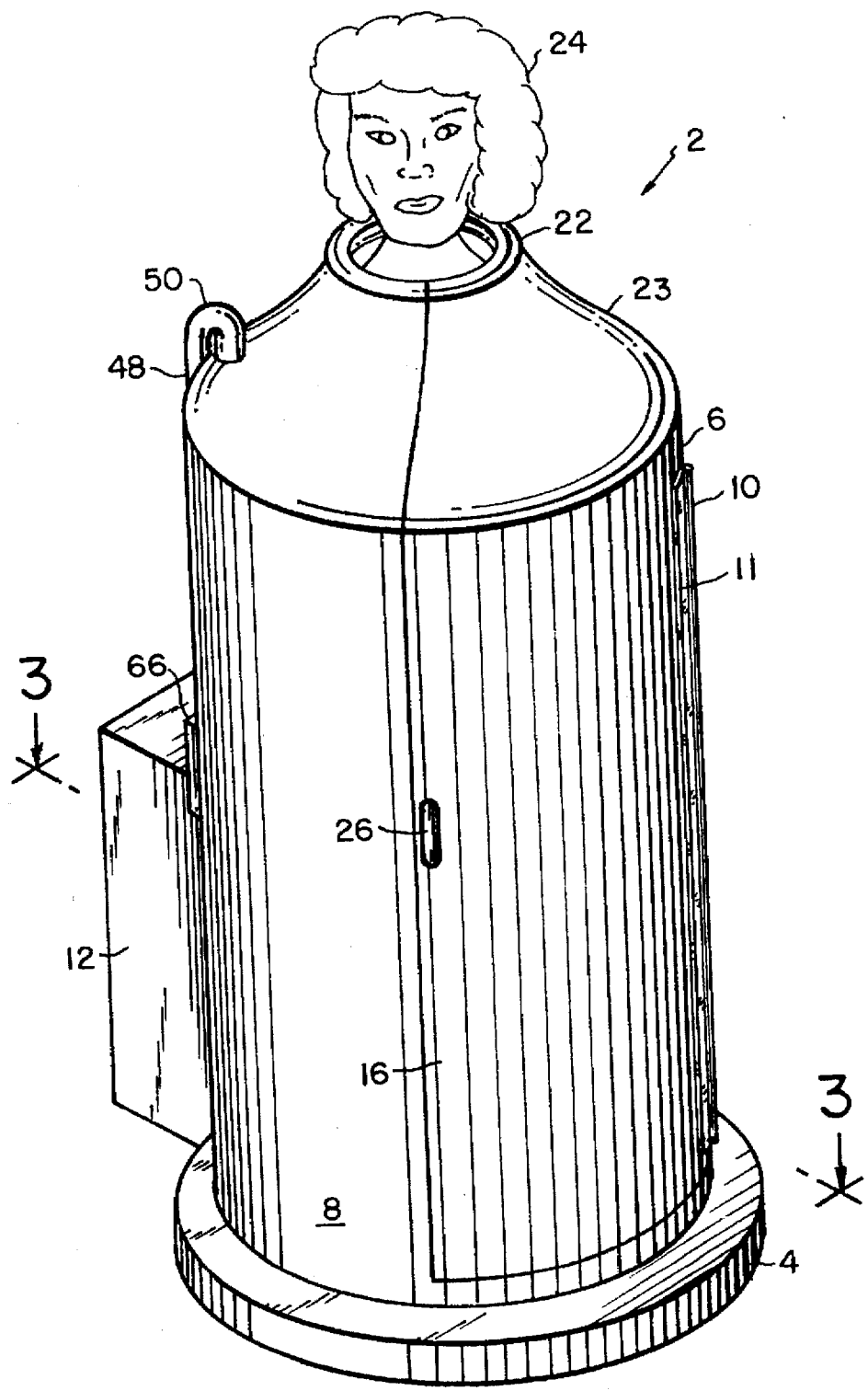
FIG. 1 is a perspective view of the apparatus with a user within the apparatus and the door of the apparatus closed.
Figure 2:
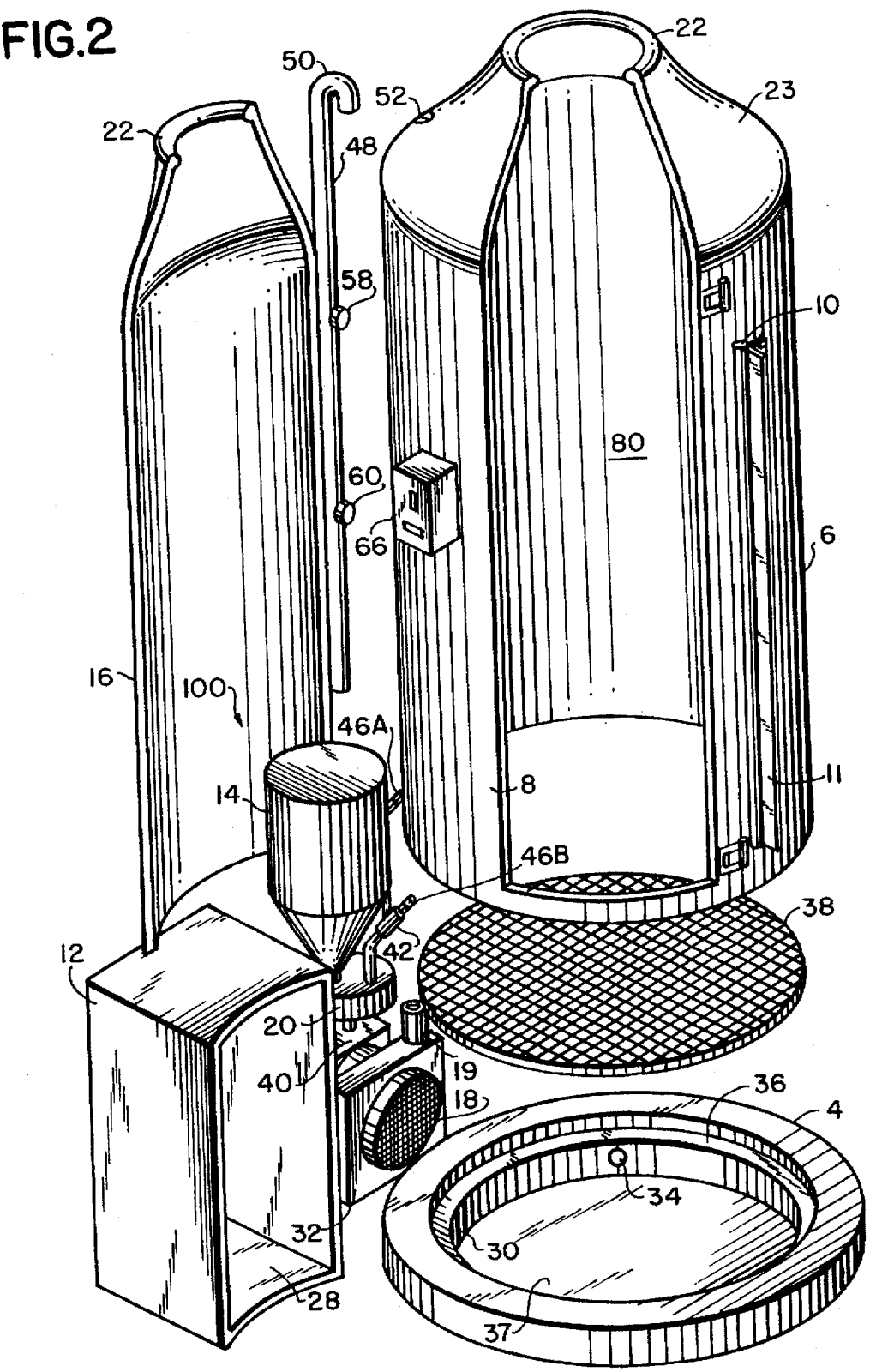
FIG. 2 is a partially expanded view of the apparatus showing the interior and the assembly of the door access panel recirculation from base and drain grate.
Figure 3:
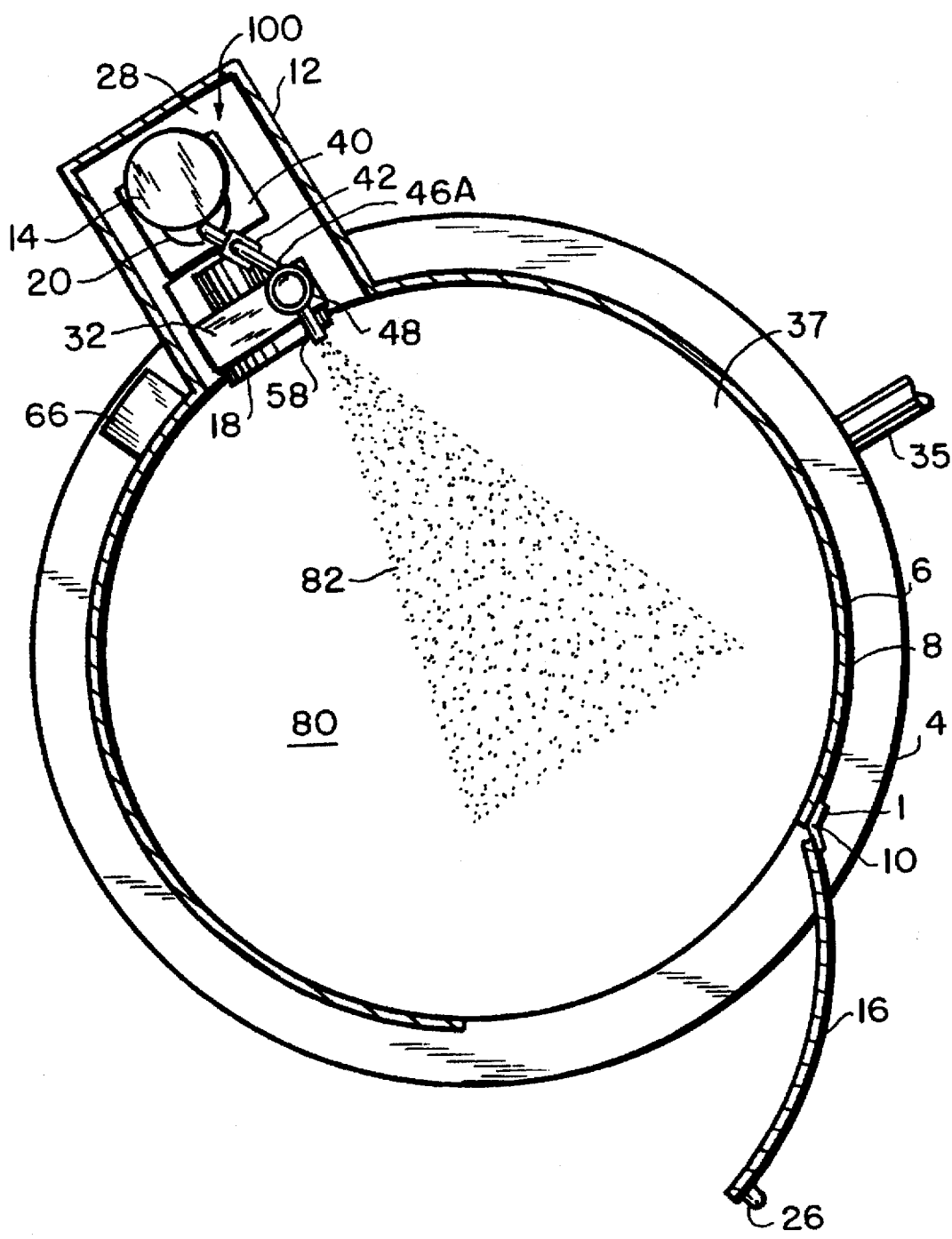
FIG. 3 is a sectional view along lines 3—3 of FIG. 1.
Figure 4:
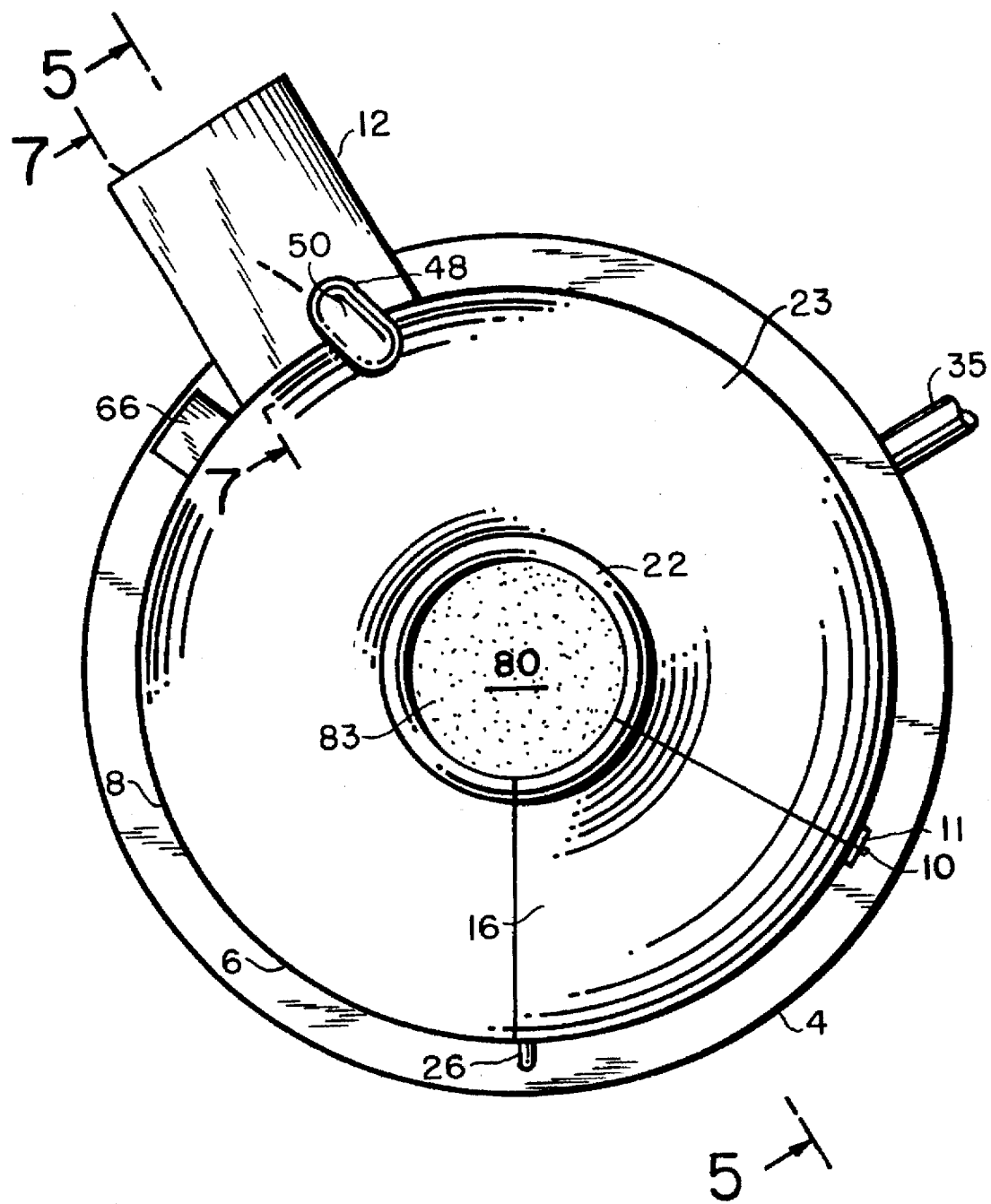
FIG. 4 is a top plain view of the apparatus.
Figure 5:
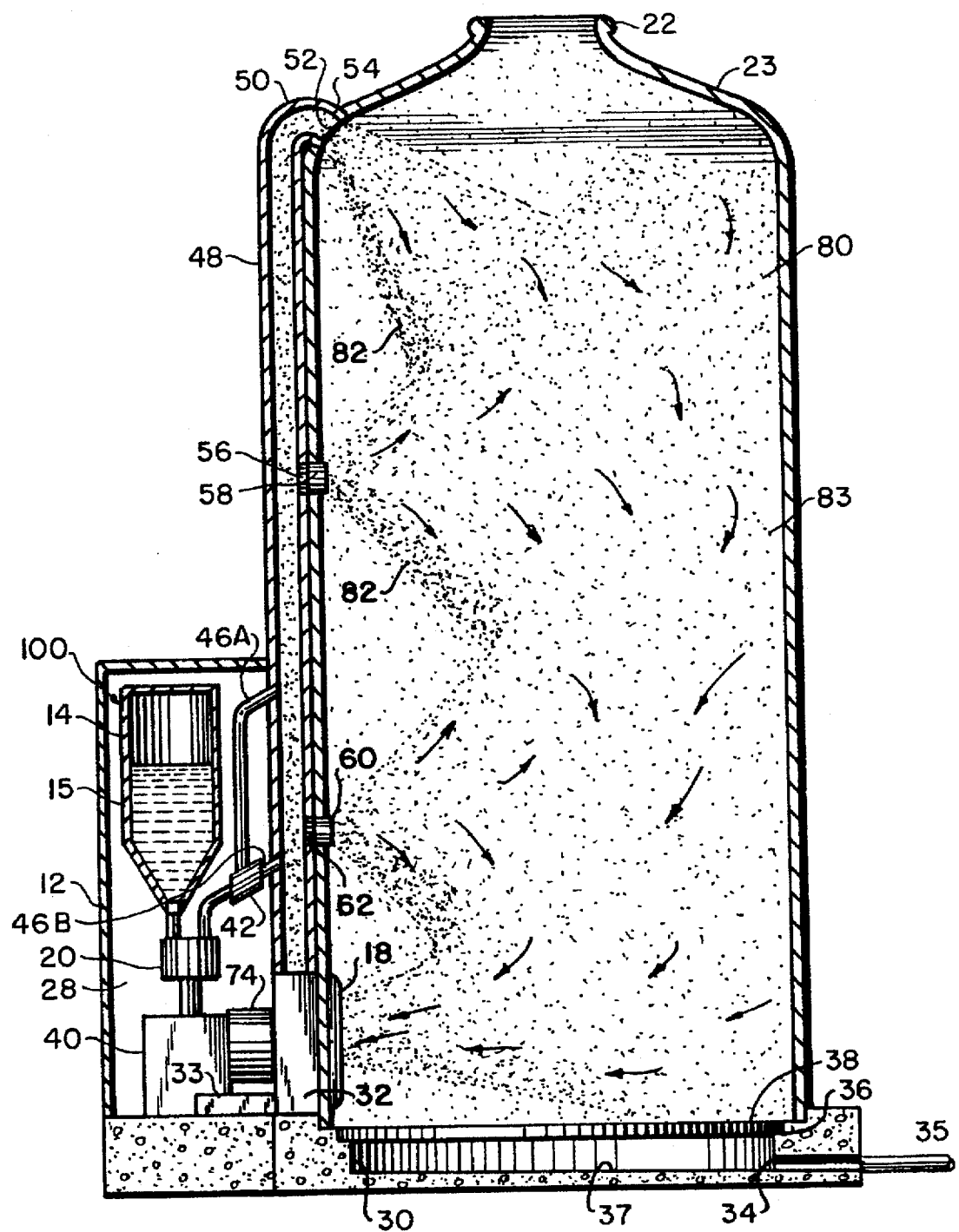
FIG. 5 is a sectional view along lines 5—5 of FIG. 4.
Figure 6:
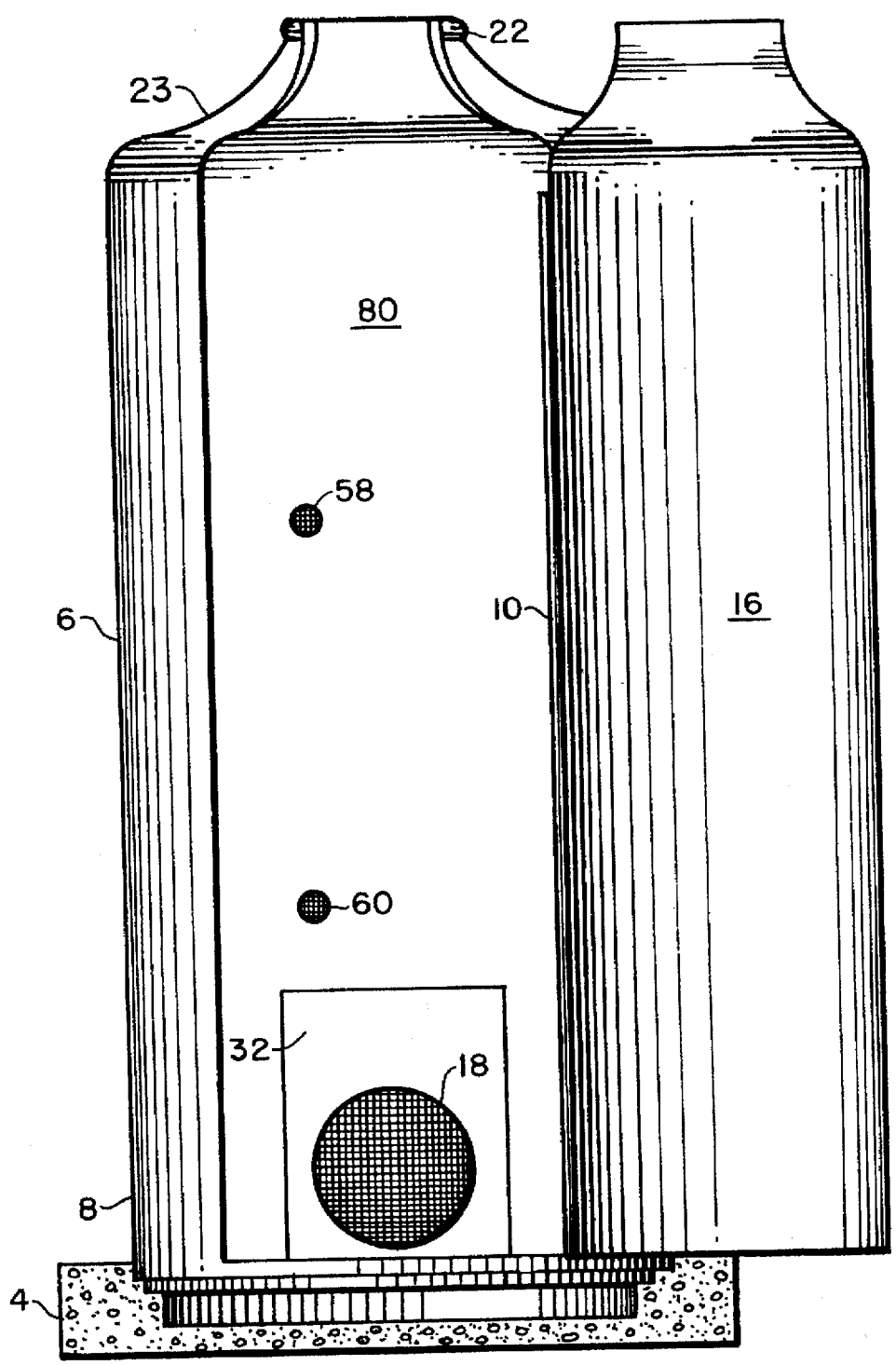
FIG. 6 is a front elevational view of the apparatus with the door open.
Figure 7:
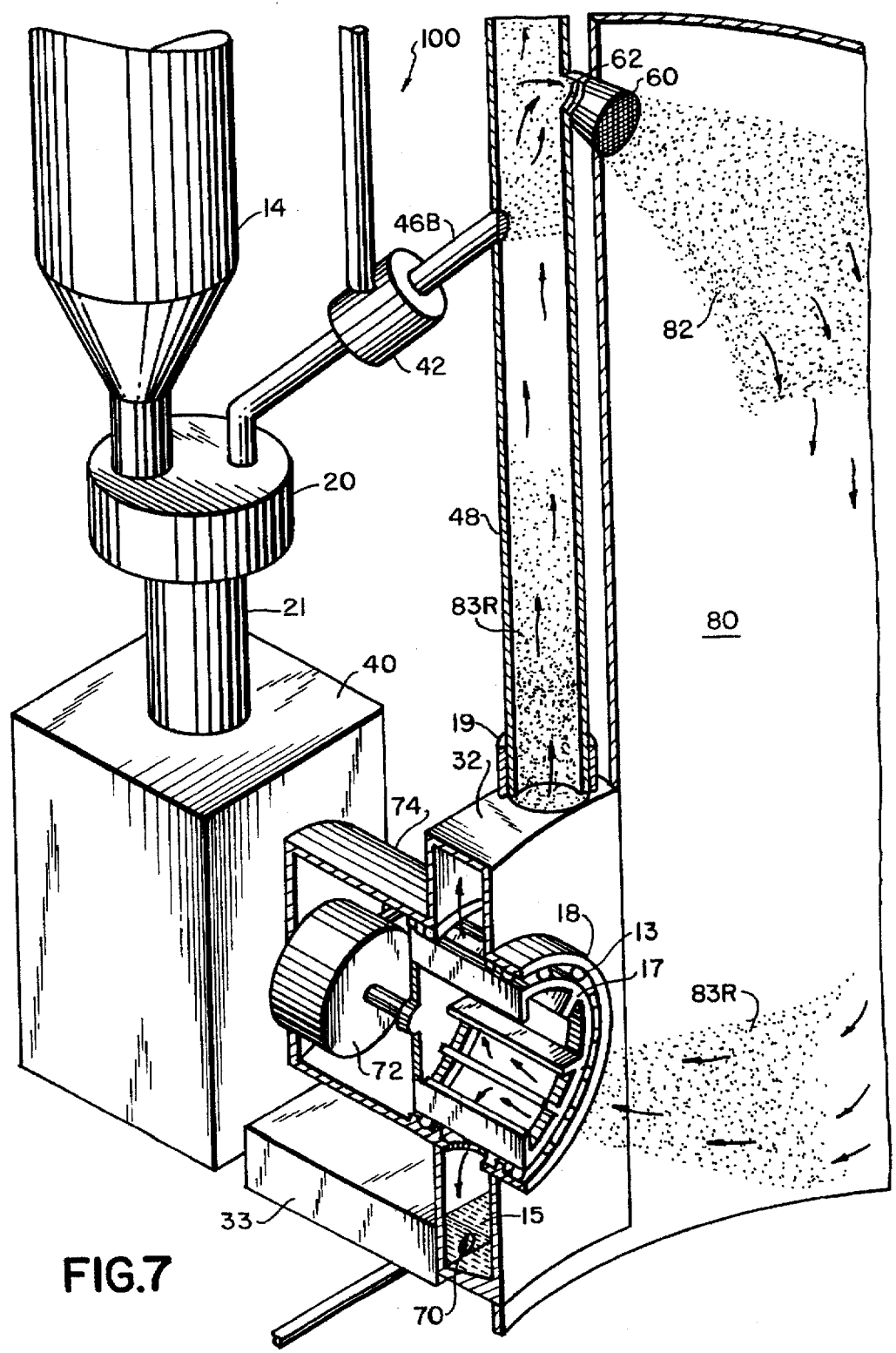
FIG. 7 is an enlarged perspective, partially in section along lines 7—7 of FIG. 4 showing details of the lotion mist recovery system.

Referring to the accompanying drawing, the apparatus of the present invention is indicated generally by the numeral 2. The apparatus 2 comprises a concrete base 4, a cylindrical enclosure 6 or tanning lotion chamber having sides 8 and a hinged swinging door 16 with handle 26. The door 16 is mounted on piano hinge 10 having leaves 11. The upper portions 23 of the sides 8 are slanted inwardly towards the collar 22.

The collar flange opening 22 has the interior rolled smoothly to provide a comfortable surface for the neck of the user 24. The diameter of enclosure 6 is approximately 3 feet and the height 4 ½ to 5 feet. Tall users may crouch slightly as necessary.

The base 4 has a recess 30 formed therein and the bottom 37 is provided at the side thereof with drain hole 34 for emptying out cleansing water or other liquids through pipe 35 when the apparatus 2 is cleaned out. A ledge 36 formed in the recess 30 in the base 4 provides a mounting for the grating 38 on which the user 24 stands.

The equipment 100 for operation of the apparatus 2 is mostly contained within the interior 28 of the accessory enclosure 12 on the side of the enclosure 6.

The pump 20 for the lotion is driven by pump motor 40 connected within enclosure 21 and lotion 15 from the supply dispenser 14 is thereby pumped to the divider 42.

The liquid lotion 15 from dispenser 14 is atomized through nozzles 46A and 46B before entering the forced air stream in tube 48. The upper end of tube 48 curves at 50 to enter opening 52 discussed below.

Thus, the pumped lotion 15 goes from the pump 20 to the divider 42 to atomizing nozzles 46A and 46B and then into tube 48.

The exterior of the sides 8 of enclosure 6 has the tube 48 secured thereto. At the top, middle, and lower portions of tube 48 spray outlets 54, and 58, and 60 respectively are in flow communication therewith through openings 52, 56, and 62 respectively in walls 8 and with the interior of the chamber 6.

The atomized lotion 82 is injected into the interior 80 of the enclosure 6 through the outlets 54, 58, and 60 respectively. Some of the mist 83 will condense as liquid and flow to the bottom 37 and exit through the outlet 34 and through the pipe 35.

The mist 83R which stays vaporized and does not condense is evacuated at the bottom of enclosure 6 through the exhaust impeller 18 by the suction created by the squirrel-cage rotor or impeller 17 within the casement 32 with bearings 13.

The recirculating impeller fan 18 to draws air and lotion mist 83R from the enclosure 6 and forces it into tube 48, there being mixed with atomized lotion 83 from nozzles 46A and 46B.

The impelling 18 device is driven by the motor 72 contained within the casing 74. The recirculated mist 83R is driven by the impeller 18 through an enclosure 32 which is connected by the collar 19 to the supply pipe 48. The recirculated lotion mist 83R is mixed and entrained with the fresh mist exiting the atomization nozzles 46A and 46B into pipe 48.

The lotion mist which condenses within the impeller enclosure drips down to the base 25 exits through the port 70 and is collected in the chamber 33.

The impeller 18 driven by the pump or motor 72 also supplies the flow and the pressure in the tube 48 which picks up the mist from the nozzles 46A and 46B.

When the user 24 desires to use the apparatus 2 he or she deposits the appropriate revenue into the token receptacle mechanism 66 and steps inside the enclosure 6. The token receptacle control 66 provides a 10 to 15 second delay to allow the user 24 to locate within the enclosure 6.

The user 24 turns around in the enclosure 6 to allow the mist 83 to be evenly distributed over his limbs and torso.

When the pumps 20 and 18 automatically turn off, after a preselected time, the user 24 there exits the enclosure 6 and then can use excess lotion 15 on his or her limbs and torso to apply to the face and neck with the palms of his or her hands.

While the invention has been described by reference to illustrative embodiment, it is not intended that the novel device be limited thereby, but that modifications thereof are intended to be included as falling within the broad spirit and scope of the foregoing disclosure, the following claims and the appended drawings.

What is claimed is:

1. Apparatus for applying suntan lotion to a human body comprising a liquid tight enclosure, a base for said enclosure having a drain aperture therein, said enclosure having a side wall, a door in said side wall of said enclosure spring biased to the closed position, lotion mist ports disposed about the exterior of said enclosure and in flow communication with a lotion distribution tube, said distribution tube in flow communication with at least one atomizing nozzle, first pump means for pumping liquid lotion from a supply dispenser associated with said first pump means to said at least one atomizing nozzle and through said at least one atomizing nozzle forming mist droplets, and into said distribution tube, and thence to said mist port outlets into the interior of said chamber, recirculating pump means for evacuating misted droplets from said base of said enclosure and recirculating those droplets into said distribution tube by means of an impeller fan, and mixing with said mist droplets from said nozzle, any lotion condensing inside said impeller being stored in a used lotion recovery reservoir, a motor for driving said pump means and said impeller fan and whereby said motor driving said pump means and said impeller fan is operated by token operated control means on the outside of the said enclosure.

* * * * *